United States Patent [19]

Strand

[11] 4,378,021

[45] Mar. 29, 1983

[54] ELECTRONIC EKG MEASUREMENT MODE SELECTION SYSTEM

[76] Inventor: Eric J. Strand, R.R. 1, Box 3001, Kasota, Minn. 56050

[21] Appl. No.: 235,654

[22] Filed: Feb. 18, 1981

[51] Int. Cl.³ .............................................. A61B 5/00
[52] U.S. Cl. .................................... 128/709; 128/710
[58] Field of Search ................................ 128/709, 710

[56] References Cited

U.S. PATENT DOCUMENTS

| | | | |
|---|---|---|---|
| 2,400,583 | 9/1947 | White | 128/709 |
| 3,517,662 | 6/1970 | Finch et al. | 128/709 |
| 3,648,689 | 3/1972 | Dominy | 128/709 |
| 3,911,905 | 10/1975 | Rossel | 128/709 |
| 4,341,225 | 7/1982 | Gallant et al. | 128/710 |

Primary Examiner—Richard J. Apley
Assistant Examiner—George Yanulis
Attorney, Agent, or Firm—Hill, Van Santen, Steadman, Chiara & Simpson

[57] ABSTRACT

In an exemplary embodiment, a measurement network at a bedside monitoring station can be sequentially stepped through a series of measurement modes either at a bedside monitoring station or at a central monitoring station. A serial in parallel out shift register has successive active positions corresponding to the successive measurement modes and may be stepped either by means of a local push button switch, or by means of a respective corresponding push button switch at the central station. At the central station, a decade counter and decoder arrangement drives a numerical readout for each local station for the purpose of representing each of the local measurement modes. A series of reset circuits couple the outputs of the first shift register stages of the respective local stations with the reset input of a corresponding decade counter such that each time the associated shift register stage is placed in an active state the counter is placed in an initial count condition. By holding a push button of the central station actuated, pulses are supplied to the corresponding local shift register at a rate of about one pulse per second so as to effect a sequencing of the measurement modes at the local station without further manual operations.

2 Claims, 5 Drawing Figures

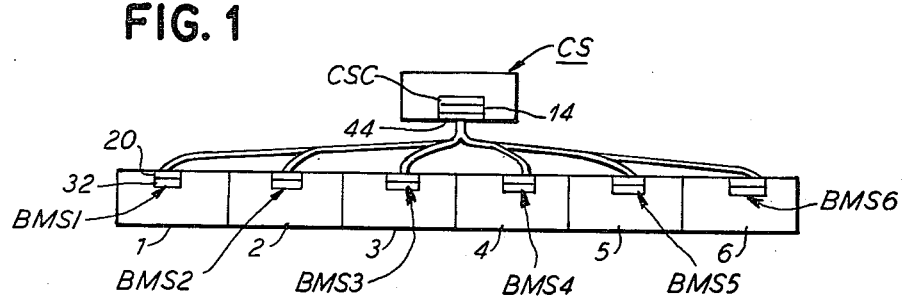
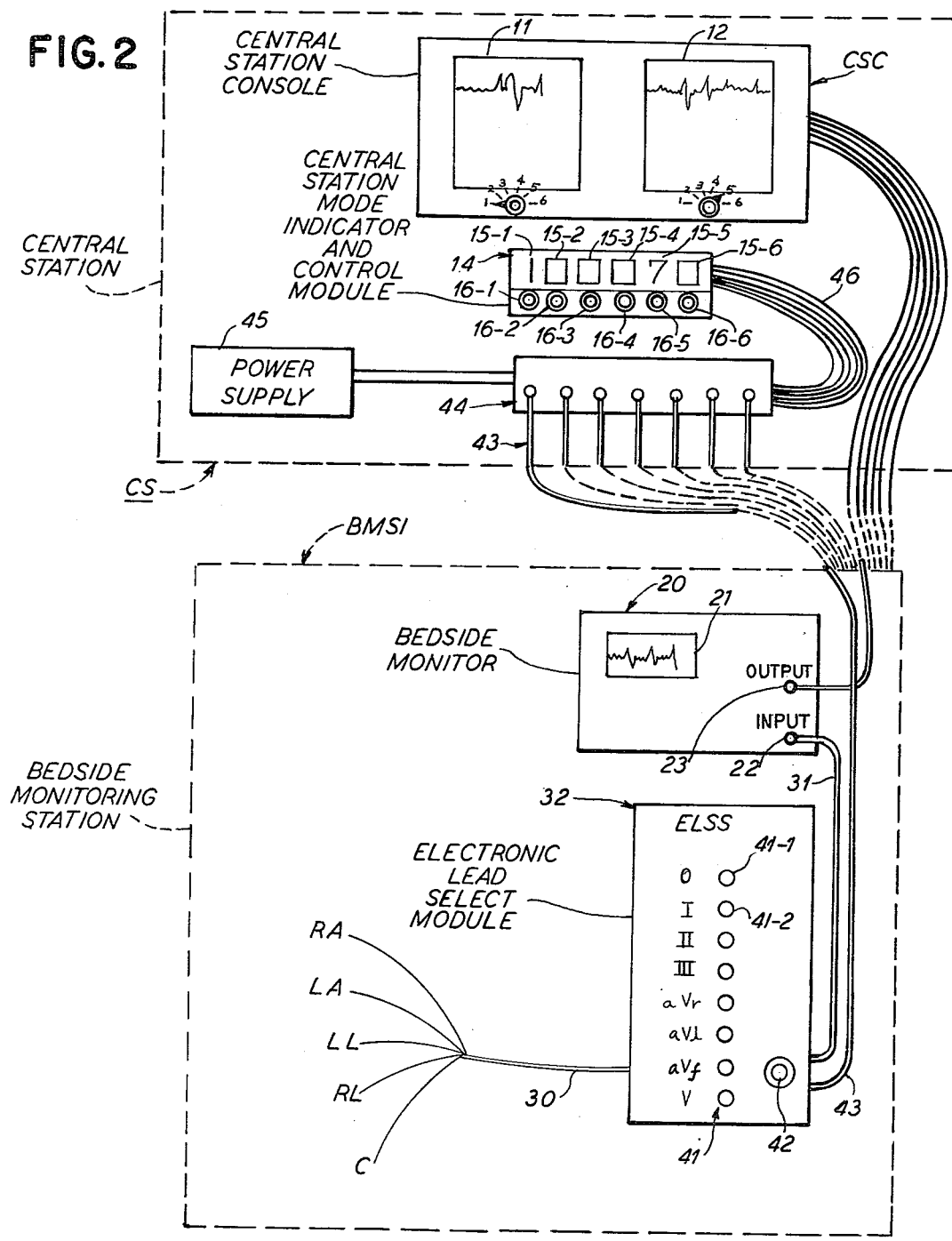

ELECTRONIC EKG MEASUREMENT MODE SELECTION SYSTEM

BACKGROUND OF THE INVENTION

In electrocardiograph measurement systems, one approach seeks to determine the characteristics of the heart from the potential distribution over the body surface. This is accomplished by the use of multiple electrodes and compensating networks based on model studies with fixed locations of the respective electrodes relative to the heart.

In a typical system there may be five electrodes to be applied at specific locations relative to the heart, and a resistance network may be employed such that there are eight different network outputs from different pairs of which respective different electrocardiograph measurement signals are to be obtained in respective different measurement modes. In one such system, the modes are conventionally designated I, II, III, aVr, aVl, aVf, and V.

SUMMARY OF THE INVENTION

It is an object of the present invention to provide an electronic mode selection system which is uniquely simple and economical and which provides an important degree of time saving for personnel concerned with the taking of a series of electrocardiograph measurements.

In accordance with a preferred embodiment of the present invention, a single push-button is associated with an electronic lead selector switch module at the bedside, the module being responsive to successive manual actuation of this switch to sequence through a predetermined set of electrocardiograph measurement modes in a predetermined order. Indicators may be provided at the module for indicating the particular measurement mode currently active. A central monitoring station may include a device for indicating the measurement mode at each of a number of patient rooms, and a remote pushbutton may be reliably incorporated into the system so as to place the measurement sequence under the control of the central station, when desired. Thus, at the central station, a number of patient rooms may be monitored in sequence simply by activating the respective associated indicator and sequence control modules and then actuating the respective remote pushbutton so as to sequence through the successive measurement modes. In this way, a skilled person at the central station can reliably obtain a sequence of electrocardiograph readings for each assigned patient without leaving the central monitoring console.

The sequencing of the successive measurement modes is to be effected by means of an integrated circuit shift register so that a reliable yet economical and compact local and remote sequencing system is achieved.

Other objects, features and advantages of the present invention will be apparent from the following detailed description taken in connection with the accompanying sheets of drawings.

BRIEF DESCRIPTION OF THE DRAWINGS

FIG. 1 is a diagrammatic view of an overall system in accordance with the present invention including a central station, and respective electronic selector switch modules at the respective patient rooms;

FIG. 2 illustrates in a diagrammatic fashion the physical appearance of the equipment of a typical system including the equipment associated with a given patient station and the central station equipment;

DETAILED DESCRIPTION OF A PREFERRED EMBODIMENT

Figure 3:
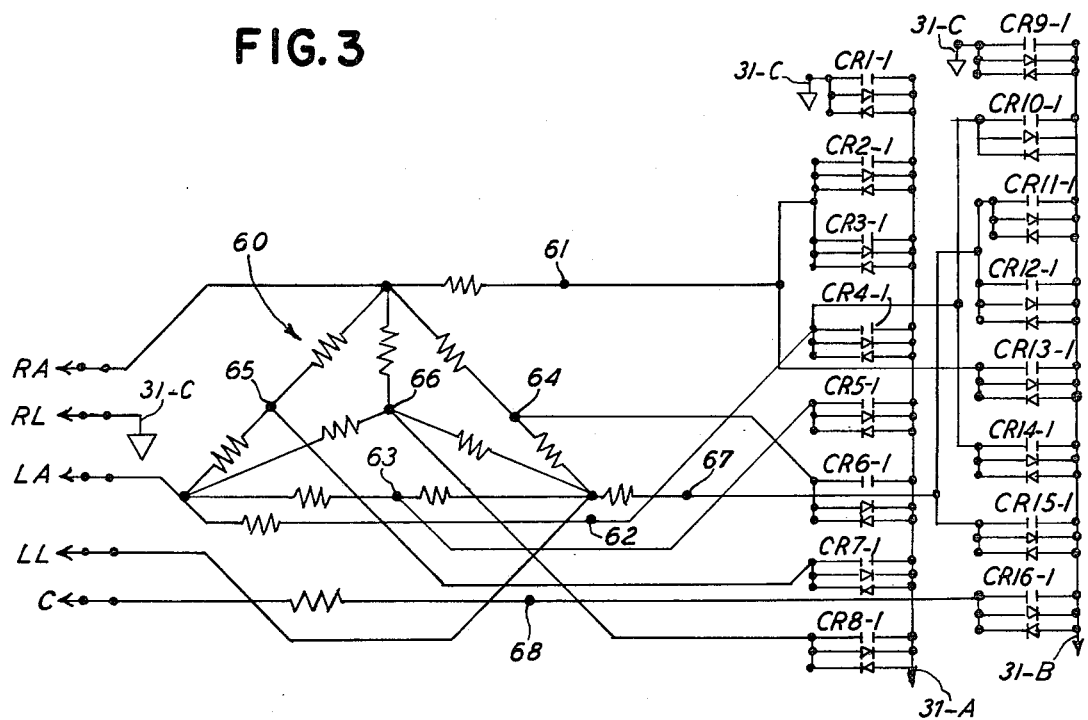
FIG. 3 is a detailed electric circuit diagram illustrating an exemplary electrocardiograph measurement system, and also indicating relay contact means for connecting respective network outputs of the system with respective channel inputs of an electrocardiograph display channel.

FIG. 1 shows an overall diagrammatic view of a typical arrangement wherein a central station CS is associated with a group of patient examination rooms such as indicated by reference numerals 1 through 6.

Referring to FIG. 2, the central station CS may include a central station console CSC with one or more oscilloscopes or monitors 11, 12 and a central station mode indicator and control module 14 with respective indicators 15-1 through 15-6, and respective associated mode selection push buttons 16-1 through 16-6.

Each of the patient examination stations such as 1 through 6, FIG. 1, may include a conventional bedside electrocardiograph monitor 20 including an oscilloscope 21, the display channel including a conventional electrocardiogram amplifier system and the oscilloscope 21, having an input as indicated at 22 for receiving various electrocardiograph measurement signals for display at 21, and having an amplifier output as indicated at 23 for transmitting the electrocardiograph measurement signals to the central station CS for display on one of the monitors of the central station console CSC. The provision for coupling a central station monitor with a selected amplifier output such as 23 may be conventional and is not further illustrated.

In a conventional electrocardiograph measurement system, there are further provided a series of leads such as the leads designated RA, LA, LL, RL, and C in FIG. 2 which are to be coupled with the patient in the vicinity of the heart in a conventional known manner.

In accordance with the teachings of the present invention there is interposed between a cable 30 containing the electrocardiograph leads and a cable 31 leading to input 22, an electronic lead selector switch module 32 which may include a series of mode indicator elements such as indicated at 41, and a local mode control pushbutton switch 42. A further cable is indicated at 43 for connecting the local module 32 with a terminal block 44 at the central station CS. Corresponding cables may be provided between the terminal block 44 and the modules at each of the respective patient rooms 1 through 6, FIG. 1. The terminal block 44 may have connected therewith a common power supply 45 for supplying five volts d.c. to each of the local modules such as 32, and also a separate conductor set (43-A, 43-B, 43-C, FIG. 4) for transmitting a pulse signal responsive to a respective central station mode select push-button 16-1 through 16-6 to the respective local module such as 32, and for controlling each respective central station measurement mode indicator 15-1 through 15-6 in accordance with the respective measurement mode currently active at the respective patient station 1 through 6. A flat ribbon type multiconductor cable is indicated at 46 for coupling the signals of the respective conductor sets to the central station mode indicator and control module 14.

FIG. 3 shows a conventional electrocardiograph measurement system including respective electrocardiograph leads designated RA, LA, LL, C and RL corresponding to the leads physically indicated in FIG. 2. The conventional configuration may include voltage limiting devices connected between respective pairs of the electrocardiograph leads and a resistance network such as indicated at 60. Also, according to conventional practice, the electrocardiograph leads RA, LA, and LL are connected with respective input terminals of a resistance network configuration which is provided with respective network outputs 61 through 67. The lead C may be connected via a resistor (of ten kilohms) and a network output 68 to one of the inputs of the display channel in one measurement mode, termed mode V. The lead RL is shown as connected to "waveform ground" via conductor 31-C of cable 31, FIG. 2.

The network 60 may be of conventional configuration, and may have resistance values arranged as follows: between LA and output 65, twenty kilohms; between output 65 and RA, twenty kilohms; between RA and output 64, twenty kilohms; between output 64 and LL, twenty kilohms; between LA and output 63, twenty kilohms; between output 63 and LL, twenty kilohms; between LA and output 62, ten kilohms; between LL and 67, ten kilohms; between RA and output 61, ten kilohms; between LA and output 66, thirty kilohms; between output 66 and LL, thirty kilohms; and between output 66 and RA, thirty kilohms.

The measurement modes to be carried out may be described as follows, having reference to the network outputs of network 60 which are to be connected to display input conductors 31-A and 31-B of FIG. 3 which form part of the cable 31 of FIG. 2:

TABLE I

Exemplary Electrocardiograph Measurement Modes

| Mode | Network Output to 31-A | Network Output to 31-B |
|---|---|---|
| I | 61 | 62 |
| II | 61 | 67 |
| III | 62 | 67 |
| aVr | 63 | 61 |
| aVl | 64 | 62 |
| aVf | 65 | 67 |
| V | 66 | 68 |

As shown in FIG. 3 each local module 32 may include respective sets of relay contacts CR1-1 through CR8-1 and CR9-1 through CR16-1 connected with the respective measurement channel conductors 31-A, 31-B which connect with respective conductors of cable 31, FIG. 2. Each pair of relay contacts may be provided with oppositely poled diodes with forward conduction voltage thresholds exceeding the normal maximum signal potentials which are permissible at output terminals 61-68, but sufficiently low so as to fully protect the patient from spurious potentials.

In a first measurement mode condition, designated lead configuration "0", the conductors 31-A and 31-B are directly connected to the waveform ground 31-C which is connected via cable 31 to the reference input of the electrocardiograph amplifier of the bedside monitor 20, FIG. 2. When lead condition zero is selected, the inputs to the ECG amplifier of bedside monitor 20 are short circuited together so that the monitor display 21 shows a straight line (input voltage equals zero) to provide a reference point by which to orient the operator at the beginning of the lead select cycle.

When relay contacts CR2-1 and CR10-1 are closed, lead condition I is established, when relay contacts CR3-1 and CR11-1 are closed, lead condition II is established, and so on for the respective modes as summarized in the foregoing Table I.

Figure 4:
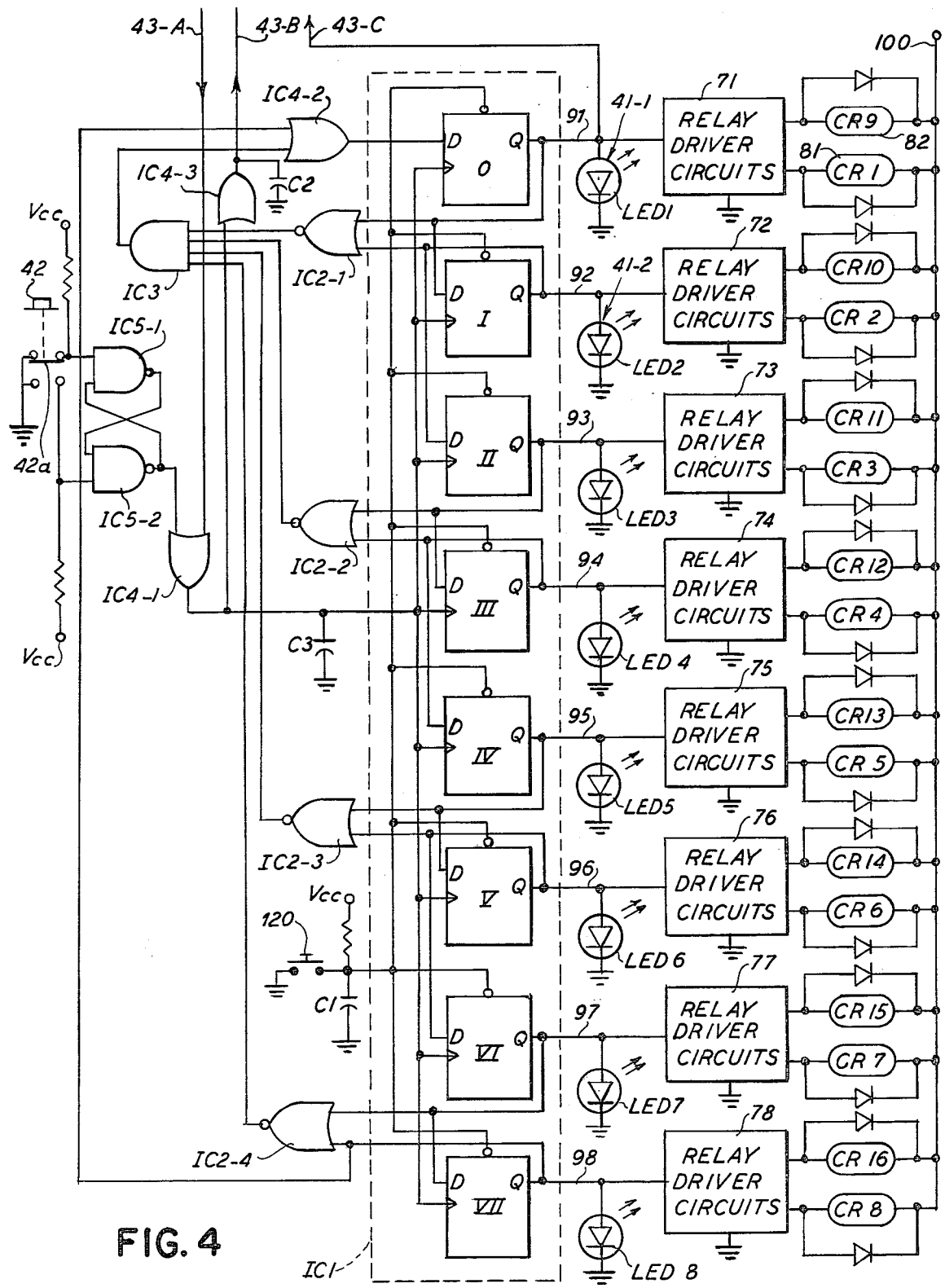
FIG. 4 is a detailed electric circuit diagram illustrating the electric circuitry for a lead selector switch module in accordance with the present invention.

FIG. 4 shows a preferred implementation for the electronic lead select module 32 for each of the bedside monitoring stations such as that indicated at BMS1 in FIG. 2. The push-button switch 42, FIG. 2, of module 32 is shown at the upper left in FIG. 4. Actuation of pushbutton switch 42, FIG. 4, places the successive stages 0 through VII of shift register IC1, FIG. 4, in the active state for supplying a logical one signal level sequentially to the successive outputs of the shift register.

FIG. 4 also illustrates relay driver circuits 71-78, each for jointly energizing a respective pair of relay coils (e.g. 81 and 82 of relays CR1 and CR9). Thus when stage 0 of the shift register IC1 is active and a logical one signal level is applied to conductor 91, relays CR1 and CR9 are actuated to close the associated contacts shown in FIG. 3 (CR1-1 and CR9-1). More specifically, the high output level at output 91 switches two 2N3904 transistors of component 71 into conducting condition to complete relay energizing circuits from voltage bus 100 through the respective relay coils 81 and 82, to the grounded emitters of such transistors. Such high output also energizes the light emitting diode LED1 for illuminating the associated measurement mode indicator which is specifically designated 41-1 in FIG. 2. Similarly, when a logical one signal level is applied to conductor 92 in FIG. 4, a second light emitting diode LED2 is energized to illuminate the second mode indicator 41-2 in FIG. 2, signifying that mode "I" is effective, with relay contacts CR2-1 and CR10-1, FIG. 3, closed. The relay driver circuits associated with conductors 92 through 98 may each correspond identically to the relay circuits of component 71. The respective indicated pairs of relays (such as CR1 and CR9, FIG. 4) are simultaneously energized to simultaneously close the correspondingly designated pairs of relay contacts (such as CR1-1 and CR9-1, FIG. 3). The respective light emitting diodes LED1 through LED8 are associated with the respective measurement mode indicators designated generally by the reference numeral 41 in FIG. 2 and serve to represent activation of the respective modes as summarized in the foregoing Table I.

To correlate FIGS. 2 and 4, the conductors of cable 43, FIG. 2, include those designated 43-A, 43-B and 43-C in FIG. 4. The push-button switch 42 which is at the upper left in FIG. 4, is shown as being coupled with a movable contact 42a, FIG. 4, which is normally biased to supply ground potential to an input of NAND gate IC5-1, but which is mechanically coupled with the push-button of switch 42 so as to be manually actuated into a position for supplying ground potential to an input of NAND IC5-2 so long as the push-button of switch 42 is held depressed. The movable contact 42a, FIG. 4, is shown as being connected to digital ground in each of its switching conditions, so that in its normal position, the bistable circuit formed by NAND gates IC5-1 and IC5-2 is in a reset condition, and a steady logical zero potential level is supplied to OR gate IC4-1.

A circuit such as indicated in FIG. 4 is associated with each of the modules 32, and is coupled with one of the indicators 15-1 through 15-6, and one of the mode selection push-buttons 16-1 through 16-6 of the module 14, FIG. 2, located at the central station CS. Thus, for example, where the circuit of FIG. 4 represents the module 32 at a patient room 1, FIG. 1, then mode selection push-button 16-1, FIGS. 2 and 5, may control the signal level at conductor 43-A, FIG. 4, such that when push-button 16-1 is momentarily depressed, a momentary logical one signal level pulse is applied to conductor 43-A. The logical one signal level pulse serves to charge capacitor C3 positively resulting in the application of a positive going voltage to the clock inputs of each of the stages 0 through VII of the shift register IC1, FIG. 4.

Figure 5:
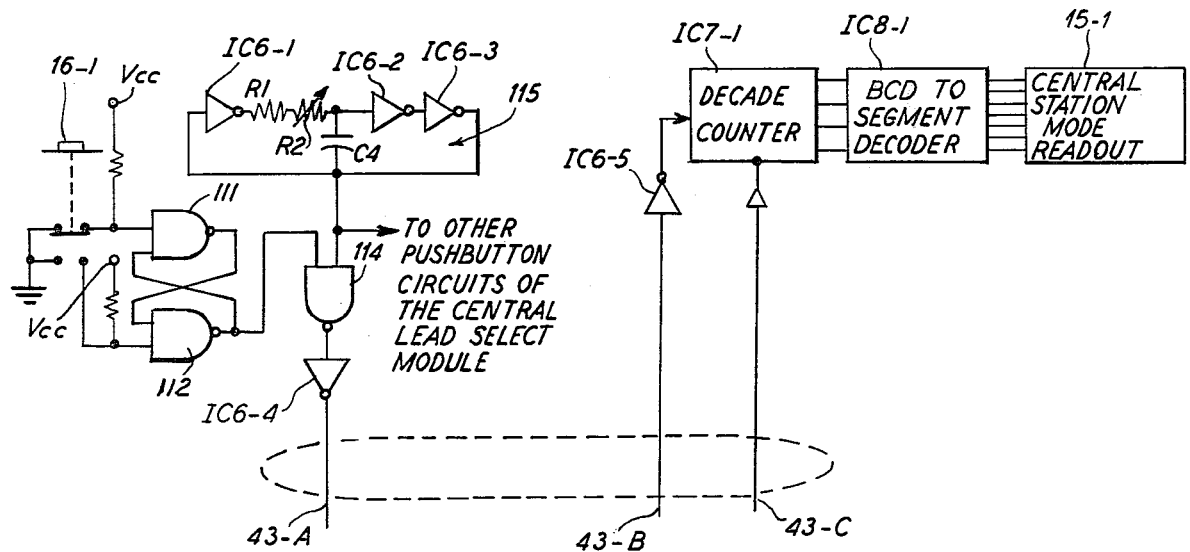
FIG. 5 is a detailed electric circuit diagram showing the electric circuitry for the central monitoring station.

As a further mode of operation, the central station operator may hold push-button 16-1 in the operated condition (against the opposition of a return spring, not shown). The bistable circuit composed of NAND gates 111 and 112 in FIG. 5 is held in a set condition as long as push-button 16-1 is held actuated, applying a logical one potential level to a first input of NAND gate 114, FIG. 5. Gate 114 is thus held enabled so that cyclical pulses from pulse circuit 115 are transmitted via gate 114 and conductor 43-A to capacitor C3. The pulse circuit 115 may supply one pulse per one and one-half seconds, so that shift register IC1 is stepped sequentially through its successive operation conditions. The result is that the display 11, FIG. 2, sequentially displays the results obtained for the successive measurement modes.

In the embodiment of FIG. 4, shift register IC1 is a serial in, parallel out shift register, and is formed as an integrated circuit, for example type 74164. When power is supplied to the circuit of FIG. 4 (from power supply 45, FIG. 2), a ground potential at capacitor C1, FIG. 4, serves to preset each of the stages 0 through VII of the shift register to the inactive condition. Thus initially the outputs of stages 0 through VII are at ground potential, and the outputs of NOR gates IC2-1, IC2-2, IC2-3 and IC2-4 are all at a logical one signal level; the output of AND gate IC3 is thus also at a logical one level so that OR gate IC4-2 will supply a logical one level to the D input of the first stage 0 of the shift register. Then the first clock pulse produced at capacitor C3 will insert a "one" into the first stage and energize indicator 41-1 and relays CR1 and CR9. A manual reset button is indicated at 120 for manually setting the shift register to the zero condition at any time.

With the shift register in the initial condition with stage 0 active, the logical one level at the output 91 of stage 0 is applied to the D input of the second stage I of the shift register. Thus when a pulse is applied to the clock inputs of the shift register, stage I is placed in the active state while the first stage 0 of the shift register is returned to the inactive condition. A similar operation results in the sequential activation of each successive stage, until stage VII is active, and each preceding stage is inactive. At this time, the logical one level at output 98 of stage VII is transmitted to the upper input of OR gate IC4-2 (located at the upper left part of FIG. 4), so that the next clock pulse again activates the first stage 0 of the shift register (while resetting stage VII to the inactive state).

FIG. 5 illustrates the manner in which the mode indicators 15-1 through 15-6 of the central station module 14, FIG. 2, display the measurement mode at the respective bedside stations. Thus when the shift register IC1, FIG. 4, is in its initial condition with stage 0 active, this stage supplies a logical one level to conductor 43-C of an associated central station circuit, for example including indicator 15-1 for the case of station BMS1, FIG. 2. The logical one level is applied via conductor 43-C, FIG. 5, to the zero set input of a decade counter IC7-1, FIG. 4. By way of example, a type 7490 decade counter may be utilized in conjunction with a type 7447 seven segment decoder IC8-1 and a seven segment LED readout element 15-1. Thus, the seven segment readout 15-1 will display a zero when the shift register IC1, FIG. 4, is in its initial condition. Each pulse applied to the clock inputs of the shift register is transmitted via NOR gate IC4-3, FIG. 4, the conductor 43-B which as shown in FIG. 5, is connected via an inverter IC6-5 with the counting input of decade counter IC7-1. Thus the counter IC7-1 is driven in step with the shift register IC1, FIG. 4, during each cycle, and the readout 15-1 will display the state of the shift register IC1 at the central station.

Exemplary Circuit Parameters

By way of example, relays CR1 through CR16, FIG. 4, may be Hamlin type HE421A0500. The shift register IC1, FIG. 4, may be an integrated circuit type 74164. The gates IC2-1 through IC2-4 may be portions of an integrated circuit type 7427. The gate IC3, FIG. 4, may be from integrated circuit type 7411. The gates IC4-1, IC4-2 and IC4-3 may be components of integrated circuit type 7432. The gates IC5-1 and IC5-2 may be from an integrated circuit type 7408. Capacitor C3, FIG. 4, may have a capacitance value of 0.01 microfarad, for example.

With respect to FIG. 5, gates such as 111, 112, and 114, may be parts of a type 7400 integrated circuit. The components IC6-1 through IC6-5 may be portions of a type 7404 integrated circuit. Resistor R1 of pulsing circuit 115 may have a value of one kilohm, while resistor R2 may be a potentiometer with a resistance value variable between 0 and 500 ohms. Capacitor C4 may have a value of 470 microfarads. As previously mentioned, decade counters such as IC7-1 may be typed 7490, while decoders such as IC8-1 may be typed 7447.

Discussion of Circuit Features

In the exemplary embodiment, an operator at the central station CS, FIG. 2, can monitor the condition of patients at any of the rooms 1 through 6, FIG. 1. With the use of the respective remote push-buttons 16-1 through 16-6 at the central station, monitoring personnel can change lead selections at any of the rooms without leaving the central monitoring console CSC, FIG. 2. There are many good reasons for this. When a patient is first admitted to Coronary Care, many people are with the patient making it difficult for the monitoring technician to get into the room to effect changes in lead selection. Another reason is that any time taken away from the central monitoring console detracts from the purpose of having monitoring personnel at the central station.

The electronic lead select modules are readily installed at the bedside monitoring stations such as BMS1, FIG. 2, by means of the plug connections of cables 30, 31, 43, FIG. 2. At the monitoring station in each room, a button such as 42 is available to sequentially change the lead configuration, and the measurement mode selected is displayed by lighting one of the indicators 41, FIG. 2.

At the central station CS, FIG. 2, one of the buttons such as 16-1 may be pressed each time it is desired to select a next measurement mode. Further, however, by holding a button such as 16-1 depressed, lead selections are changed automatically approximately every 1.5 seconds. The condition of the electronic lead select module 32 at the bedside station is reliably represented by displaying a number (0 through 7) on the associated indicator such as 15-1, FIG. 2.

The five volts d.c. necessary for powering the system is obtained from power supply 45 at the central station, FIG. 2. Wiring to each bedside monitoring station, such as via cable 43, FIG. 2, includes two wires for carrying the five volt d.c. power, one wire 43-A, FIG. 5, for carrying the control pulse from the central station for lead selection, and two wires 43-B and 43-C, FIG. 5, for controlling the display of measurement mode at the central station.

It will be apparent that many modifications and variations may be effected without departing from the scope of the novel concepts and teachings of the present invention.

I claim as my invention:

1. A medical lead selection system comprising:
   (a) a series of electronic lead select modules for disposition at respective bedside monitoring stations,
   (b) each electronic lead select module having:
      (b1) a series of input leads for electrical coupling with a patient for receiving respective electrical activity signals,
      (b2) a measuring network having respective network inputs connected with the respective input leads, and having network outputs for supplying a predetermined set of electrical measurement signals,
      (b3) a measurement display channel having first and second measurement channel conductors for selective connection with respective different pairs of the network outputs to receive respective different ones of said predetermined set of electrical measurement signals,
      (b4) respective relay means having a first series of relay contacts interposed between different network outputs and said first measurement channel conductor, and having a second series of relay contacts interposed between different network outputs and said second measurement channel conductor,
      (b5) pulse responsive shift register means having pulse input means and a series of bistable shift register stages with respective logic signal outputs, said pulse responsive shift register means having setup means for placing a first one of said shift register stages in an active state in response to a pulse at said pulse input means while each of the remaining shift register stages is in an inactive state, and being responsive thereafter to respective control pulses supplied to said pulse input means to place successive ones of said bistable shift register stages of said series into an active state while a preceding one of said shift register stages is returned to said inactive state, thereby to activate successive ones of said logic signal outputs one at a time,
      (b6) circuit means coupling respective logic signal outputs with the respective relay means for controlling actuation thereof such that successive control pulses supplied to said pulse input means of said pulse responsive shift register means activate respective relay contacts of said first and second series of relay contacts to supply the respective different electrical measurement signals of said predetermined set to said measurement display channel in a predetermined sequence, and
      (b7) manually controlled pulser means connected with said pulse input means and operative in response to manual actuation thereof to effect the supply of successive pulses to said pulse responsive shift register means, whereby manual actuation of the manually controlled pulser means effects the display of the predetermined set of electrical measurement signals in said predetermined sequence,
   (c) a central lead select module for disposition at a central station and for coupling with each of said electronic lead select modules,
   (d) said central lead select module comprising:
      (d1) a series of matrix display elements each matrix display element being operable for displaying a sequence of indications for representing the respective different ones of said predetermined set of electrical measurement signals,
      (d2) a series of counter stages each having a counter input responsive to successive actuating pulses to assume sequential count conditions, each having a counter output coupled with a respective one of said matrix display elements for controlling the same to display said sequence of indications in response to sequential count conditions of the respective corresponding counter stage, and said counter stages each having a reset input responsive to a resetting signal to assume an initial count condition,
      (d3) a series of respective manually controlled pulsers assigned to respective ones of said series of matrix display elements, and being operative for supplying respective control pulses in response to respective manual actuations,
   (e) circuit means for coupling each of said manually controlled pulsers with the pulse input means of one of said pulse responsive shift register means, such that successive manual actuations of one of said manually controlled pulsers is operative to successively actuate an associated one of said shift register means so as to activate successive ones of the logic signal outputs thereof,
   (f) a series of control pulse monitor circuits each coupling the pulse input means of one of said shift register means with the counter input of one of said series of counter stages such that each control pulse transmitted to the pulse input means of the one of said shift register means is also transmitted via the associated monitor circuit to the associated one of said series of counter stages, and
   (g) a series of reset circuits each coupling the logic signal output of a first shift register stage of an associated one of the shift register means with the reset input of a corresponding one of said series of counter stages such that each time the associated shift register means has its first shift register stage placed in an active state the corresponding one of said series of counter stages is placed in its initial count condition.

2. A medical lead selection system according to claim 1, with said central lead select module further having a common pulse generator operating at a rate of about one pulse per second, and respective AND gates each having one input connected with said common pulse generator and having a second input controlled by one of the respective manually controlled pulsers of the central lead select module and having respective outputs coupled with the respective pulse inputs means of the respective shift register means of said lead select modules, such that holding one of said manually controlled pulsers in the actuated condition enables the associated AND gate to transmit pulses from said common pulse generator at said rate of about one pulse per second to the associated shift register means and thereby to effect the display of the electrical measurement signals in said predetermined sequence so long as the pulser is held in the actuated condition.

* * * * *